US009629683B2

(12) United States Patent
Hatta (10) Patent No.: US 9,629,683 B2
(45) Date of Patent: Apr. 25, 2017

(54) OPERATION INPUT DEVICE AND MASTER-SLAVE SYSTEM

(71) Applicant: OLYMPUS CORPORATION, Tokyo (JP)

(72) Inventor: Izumi Hatta, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/713,702

(22) Filed: May 15, 2015

(65) Prior Publication Data

US 2015/0245874 A1  Sep. 3, 2015

Related U.S. Application Data

(63) Continuation of application No. PCT/JP2014/054099, filed on Feb. 14, 2014.
(Continued)

(51) Int. Cl.
| | |
|---|---|
| *G05B 19/04* | (2006.01) |
| *G05B 19/18* | (2006.01) |
| *A61B 19/00* | (2006.01) |
| *G05G 1/04* | (2006.01) |
| *G05B 15/02* | (2006.01) |

(Continued)

(52) U.S. Cl.
CPC .......... *A61B 19/2203* (2013.01); *A61B 34/30* (2016.02); *A61B 34/37* (2016.02); *A61B 34/74* (2016.02); *A61B 34/77* (2016.02); *G05B 15/02* (2013.01); *G05G 1/04* (2013.01); *A61B 2034/301* (2016.02); *A61B 2034/742* (2016.02)

(58) Field of Classification Search
CPC combination set(s) only.
See application file for complete search history.

(56) References Cited

U.S. PATENT DOCUMENTS 4,837,734 A * 6/1989 Ichikawa ............. G05B 19/427
414/1
4,950,116 A * 8/1990 Nishida .................... B25J 13/02
414/5
(Continued)

FOREIGN PATENT DOCUMENTS

CN   201562907 U   8/2010
JP   H05-076482 A   3/1993
(Continued)

OTHER PUBLICATIONS

International Search Report dated May 27, 2014 issued in PCT/JP2014/054099.
(Continued)

*Primary Examiner* — Bhavesh V Amin
(74) *Attorney, Agent, or Firm* — Scully, Scott, Murphy & Presser, P.C.

(57) ABSTRACT

Provided is an operation input device including a base member; a grip that is gripped by an operator and that is moved relative to the base member; a coupling portion that couples the grip to the base portion in a pivotable manner; and a scaling-ratio changing mechanism that changes an amount by which the grip is moved with respect to a pivoting angle of the coupling portion, and an object thereof is to enable switching operation between a coarse movement and a fine movement by using the same operation.

3 Claims, 9 Drawing Sheets

Related U.S. Application Data (60) Provisional application No. 61/772,647, filed on Mar. 5, 2013.

(51) Int. Cl.
*A61B 34/37* (2016.01)
*A61B 34/00* (2016.01)
*A61B 34/30* (2016.01)

(56) References Cited

U.S. PATENT DOCUMENTS

| | | | | |
|---|---|---|---|---|
| 5,047,701 | A * | 9/1991 | Takarada | B25J 9/161 |
| | | | | 318/568.16 |
| 5,105,367 | A * | 4/1992 | Tsuchihashi | B25J 3/04 |
| | | | | 700/264 |
| 5,339,799 | A * | 8/1994 | Kami | A61B 34/76 |
| | | | | 600/109 |
| 5,410,638 | A * | 4/1995 | Colgate | B25J 17/0216 |
| | | | | 700/260 |
| 5,876,325 | A * | 3/1999 | Mizuno | A61B 1/00048 |
| | | | | 600/102 |
| 6,212,443 | B1 * | 4/2001 | Nagata | G05B 19/423 |
| | | | | 318/568.13 |
| 6,496,756 | B1 * | 12/2002 | Nishizawa | B25J 9/1689 |
| | | | | 700/260 |
| 6,793,653 | B2 * | 9/2004 | Sanchez | A61B 19/2203 |
| | | | | 600/102 |
| 6,810,281 | B2 * | 10/2004 | Brock | A61B 5/04 |
| | | | | 600/407 |
| 7,331,967 | B2 * | 2/2008 | Lee | A61B 34/71 |
| | | | | 600/407 |
| 7,844,474 | B2 * | 11/2010 | Barth | A61B 6/032 |
| | | | | 705/3 |
| 8,258,917 | B2 * | 9/2012 | Cai | G06F 3/0346 |
| | | | | 180/167 |
| 8,755,864 | B2 * | 6/2014 | Hauck | A61B 5/6885 |
| | | | | 600/424 |
| 2010/0318100 | A1 | 12/2010 | Okamoto et al. | |
| 2011/0152882 | A1 * | 6/2011 | Wenderow | A61F 2/95 |
| | | | | 606/130 |
| 2012/0071752 | A1 * | 3/2012 | Sewell | A61B 6/12 |
| | | | | 600/424 |
| 2012/0209293 | A1 * | 8/2012 | Carlson | A61B 19/2203 |
| | | | | 606/130 |
| 2013/0318100 | A1 * | 11/2013 | Cofino | G06F 17/30684 |
| | | | | 707/748 |

FOREIGN PATENT DOCUMENTS

| | | |
|---|---|---|
| JP | H06-074660 U | 10/1994 |
| JP | H07-328016 A | 12/1995 |
| JP | H08-071072 A | 3/1996 |
| JP | H08-224248 A | 9/1996 |
| JP | H11-095851 A | 4/1999 |
| JP | H11-184544 A | 7/1999 |
| JP | H11-191013 A | 7/1999 |
| JP | 2000-505328 A | 5/2000 |
| JP | 2002-212976 A | 7/2002 |
| JP | 3339953 B2 | 10/2002 |
| JP | 4608601 B2 | 1/2011 |
| JP | 2012-115471 A | 6/2012 |
| WO | 2009/120948 A2 | 10/2009 |
| WO | 2010/055745 A1 | 5/2010 |
| WO | 2012/167043 A2 | 12/2012 |

OTHER PUBLICATIONS

English translation of JP H07-194609, dated Aug. 1, 1995.
Extended Supplementary European Search Report dated Sep. 21, 2016 in European Patent Application No. 14 76 0107.4.

* cited by examiner

OPERATION INPUT DEVICE AND MASTER-SLAVE SYSTEM

CROSS-REFERENCE TO RELATED APPLICATIONS

This is a continuation of International Application PCT/JP2014/054099, with an international filing date of Feb. 14, 2014, which is hereby incorporated by reference herein in its entirety. This application claims the benefit of U.S. Provisional Patent Application No. 61/772,647, the content of which is incorporated herein by reference.

TECHNICAL FIELD

The present invention relates to an operation input device and a master-slave system.

BACKGROUND ART

In the related art, there is a known master input device of a master-slave system, which has a similar shape to a slave device (for example, see Patent Literature 1).

This master input device has a plurality of joints, and bending movement of corresponding bending portions of the slave device is performed in a manner proportional to rotational operation inputs for the respective joints.

CITATION LIST

Patent Literature

{PTL 1} Publication of Japanese Patent No. 4608601

SUMMARY OF INVENTION

The present invention provides the following solutions.

An aspect of the present invention provides an operation input device including a base member; a grip that is gripped by an operator and that is moved relative to the base member; a coupling portion that couples the grip to the base portion in a pivotable manner; and a scaling-ratio changing mechanism that changes an amount by which the grip is moved with respect to a pivoting angle of the coupling portion.

DESCRIPTION OF EMBODIMENTS

In the following, a master device (operation input device) 2 and a master-slave system 1 according to a first embodiment of the present invention will be described below with reference to the drawings.

Figure 1:
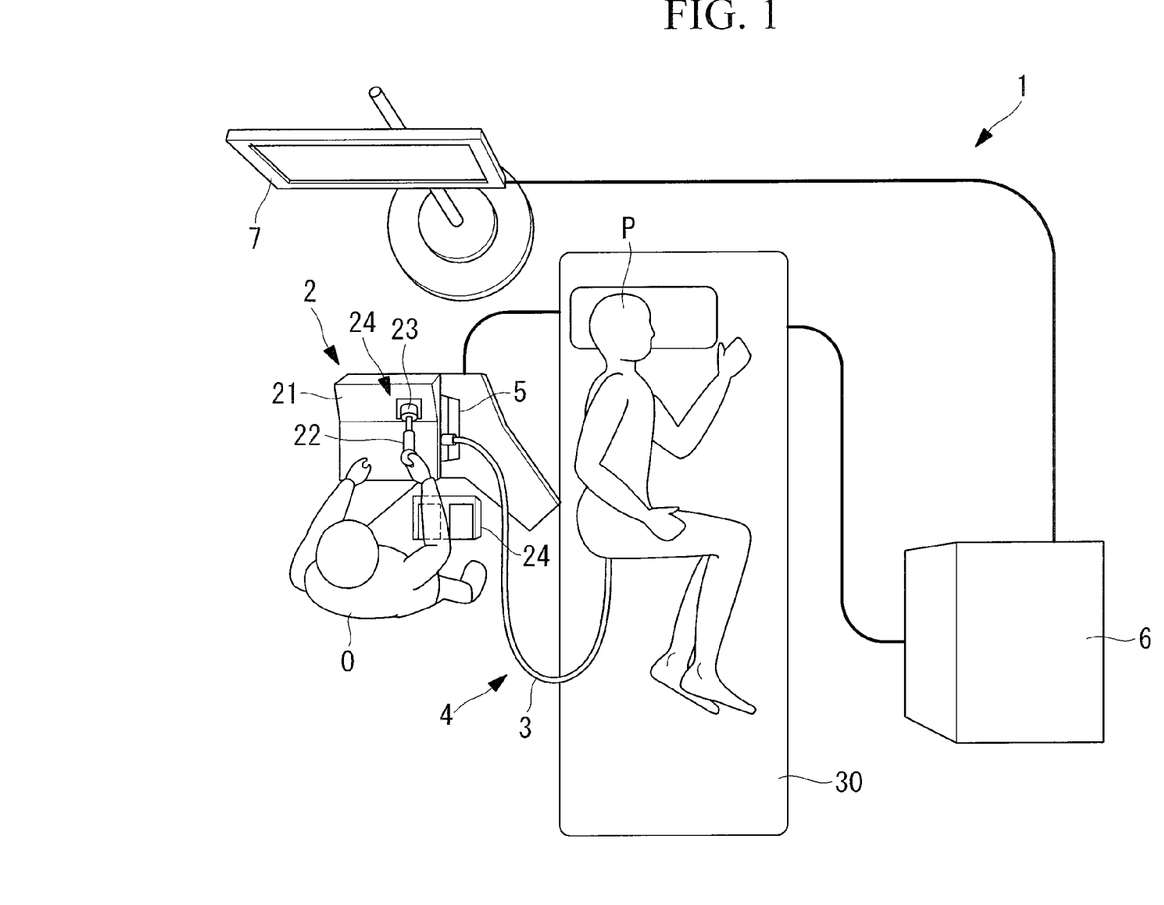
FIG. 1 is a diagram showing the overall configuration of a master-slave system according to a first embodiment of the present invention.

As shown in FIG. 1, the master-slave system 1 according to this embodiment is an endoscope system and is provided with a master device (operation input device) 2 that is operated by an operator O, an endoscope 4 that serves as a slave device, a driving portion 5 that drives the endoscope 4, a control portion 6 that controls the driving portion 5, and a display portion 7 that displays an image acquired by the endoscope 4.

The endoscope 4 has a flexible inserted portion 3 that is inserted into the body of a patient P, for example, a soft organ such as the large intestine or the like.

The driving portion 5 drives the inserted portion 3 at the proximal end thereof to achieve inserting movement of the inserted portion 3 of the endoscope 4, bending movement of the distal end of the inserted portion 3, twisting movement of the inserted portion 3, and so forth.

Figure 2:
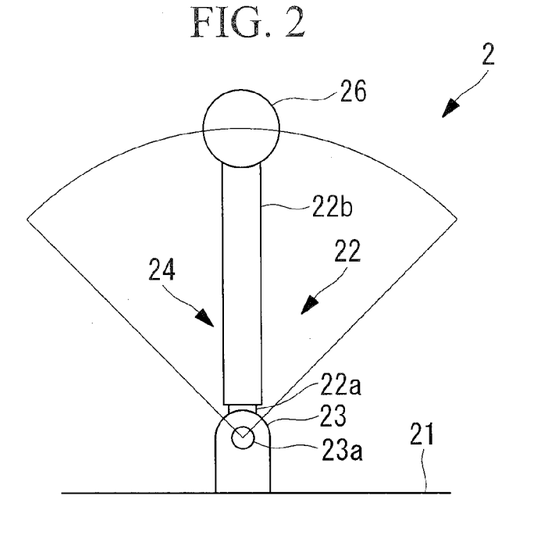
FIG. 2 is a front view of an operation input device according to the first embodiment of the present invention, showing a case in which a scaling ratio is decreased.

As shown in FIGS. 1 and 2, the master device 2 has an operation table (base member) 21 that is fixed to the floor, a lever 22 that is gripped by the operator O, a joint portion 23 that couples the lever 22 to the operation table 21 in a pivotable manner, a scaling-ratio changing mechanism 24 provided in the lever 22, and a footswitch 25 disposed on the floor.

As shown in FIG. 1, an assistant (not shown) lays the patient P down on a surgical table 30 disposed closer to the operating unit 2 and performs appropriate procedures such as sterilization, anesthesia, and so forth.

The operator O instructs the assistant to introduce the inserted portion 3 into the large intestine from the anus of the patient P. The operator O operates the lever 22 to appropriately bend a bending portion of the inserted portion 3.

As shown in FIG. 2, the lever 22 is formed as a single straight rod and is provided with the grip 26, which is gripped by the operator O, at the distal end thereof. Portions of the lever 22 excluding the grip 26 and the joint portion 23 form a coupling portion that couples the grip 26 to the base portion 21 in a pivotable manner.

The joint portion 23 couples the lever 22 to the operation table 21 so as to be pivotable about two substantially horizontal axes 23*a* (only one of which is illustrated) that are perpendicular to each other and that are located at the base of the lever 22. In addition, an angle sensor (not shown) that detects pivoting angles of the lever 22 about the two axes 23*a* is disposed at the joint portion 23.

The scaling-ratio changing mechanism 24 is constituted of an extending/contracting mechanism that allows the lever 22 to be extended/contracted in the longitudinal direction thereof. The extending/contracting mechanism is formed by, for example, configuring the lever 22 as a double cylinder and is provided with a first cylindrical portion 22a that is coupled with the joint portion 23 and a second cylindrical portion 22b that has the first cylindrical portion 22a fitted inside thereof and that is disposed so as to be movable in the longitudinal direction with respect to the first cylindrical portion 22a. The grip 26 is provided on the second cylindrical portion 22b.

The operation of the thus-configured master device 2 according to this embodiment will be described below.

In order to observe and perform treatment inside a body cavity by using the endoscope 4 in a state in which the endoscope 4 is inserted into the body cavity, the operator O grips the grip 26 provided on the lever 22 of the master device 2 and applies a force in a direction that intersects the lever 22 while observing the condition of the body interior captured by the endoscope 4 via the display portion 7.

By doing so, the lever 22 pivots about the axis 23a of the joint portion 23 in the direction in which the force is applied, and the angle sensor provided at the joint portion 23 detects the pivoting angle of the lever 22. In other words, this pivoting-angle signal of the lever 22 is output as an operation input level of the master device 2.

The control portion 6 receives the operation input level output from the master device 2, converts it to a movement-angle command signal for the bending portion of the endoscope 4, and drives the endoscope 4. By doing so, the bending portion of the endoscope 4 is bent by an angle corresponding to the pivoting angle of the lever 22 in a predetermined' direction associated with the pivoting direction of the lever 22.

Figure 3:
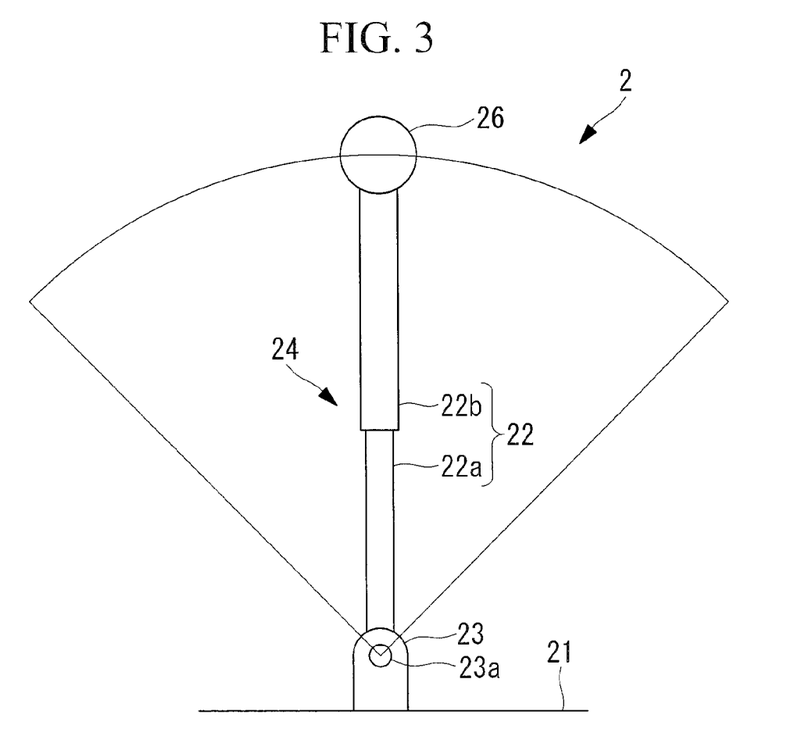
FIG. 3 is a front view of the operation input device in FIG. 2, showing a case in which the scaling ratio is increased.

In this case, when detailed observation or treatment needs to be performed by finely moving the endoscope 4, the operator O increases the length of the lever 22 in the longitudinal direction, as shown in FIG. 3, by actuating the extending/contracting mechanism, that is, the scaling-ratio changing mechanism 24. In other words, the second cylindrical portion 22b is slid in the longitudinal direction with respect to the first cylindrical portion 22a. By doing so, because the grip 26 is moved in the direction away from the joint portion 23, the amount by which the grip 26 is moved about the axis 23a of the joint portion 23 is increased.

Specifically, comparing a state in which the length of the lever 22 is decreased and a state in which the length of the lever 22 is increased, in order to make the joint portion 23 pivot by the same pivoting angle, the grip 26 must be moved by a greater amount in the state in which the length of the lever 22 is increased. Because of this, an actuation level of the bending portion of the endoscope 4 resulting from a unit amount by which the grip 26 is moved by the operator O is decreased, and thus, it is possible to move the endoscope 4 finely.

In contrast, when the bending portion of the endoscope 4 needs to be moved coarsely, the length of the lever 22 is decreased in the longitudinal direction, as shown in FIG. 2, by actuating the extending/contracting mechanism, that is, the scaling-ratio changing mechanism 24. By doing so, because the grip 26 is moved in the direction toward the joint portion 23, it is possible to decrease the amount by which the grip 26 is moved about the axis 23a of the joint portion 23, and thus, it is possible to move the bending portion of the endoscope 4 coarsely.

As described above, with the master device 2 and the master-slave system 1 according to this embodiment, by actuating the scaling-ratio changing mechanism 24, it is possible to switch between fine movement and operation of the endoscope 4 in a simple manner, and an advantage is afforded in that it is possible to efficiently perform observation or treatment by achieving more detailed observation and treatment, quicker movement of the endoscope 4, and so forth.

Note that, in this embodiment, although only one axis 23a is illustrated for the joint portion 23 for the purpose of simplifying the illustration, the joint portion 23 has two axes that are perpendicular to each other. Accordingly, the lever 22 can be pivoted not only in the direction parallel to the plane of the drawings, as shown in FIGS. 2 and 3, but the lever 22 can also be pivoted in the direction that intersects the plane of the drawings. In addition, the master device 2 also allows an operation in which the lever 22 is pivoted about the axis thereof, and the distal end portion of the endoscope 4 can be rotated about the axis thereof by means of this operation.

Next, a master device 10 according to a second embodiment of the present invention will be described below with reference to the drawings.

In describing this embodiment, portions having the same configurations as those of the master device 2 and the master-slave system 1 according to the first embodiment described above will be assigned the same reference signs, and descriptions thereof will be omitted.

Figure 4:
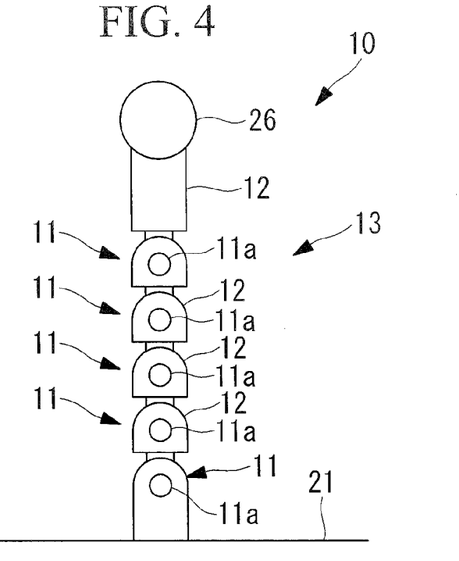
FIG. 4 is a front view of an operation input device according to a second embodiment of the present invention.

As shown in FIG. 4, a master device 10 according to this embodiment is provided with, as the coupling portion, a plurality of joint portions 11 that are arranged in series, and has a lever 13 in which adjacent joint portions 11 are coupled by linkages 12.

In addition, the individual joint portions 11 are provided with locking mechanisms (not shown) that lock pivoting of the joint portions 11. In addition, the individual joint portions 11 are configured such that the linkages 12 can be pivoted separately about two axes 11a (only one of which is illustrated) that are perpendicular to each other.

Figure 6:
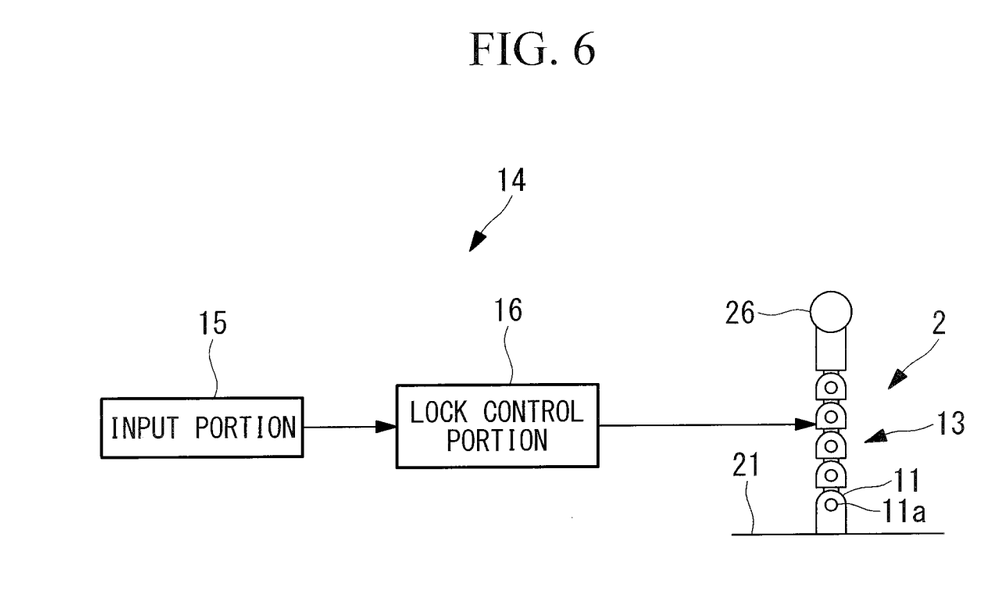
FIG. 6 is a block diagram showing an example of a scaling-ratio changing mechanism provided in the operation input device in FIG. 4.

In this embodiment, an input portion 15 for inputting a scaling ratio and a lock control portion 16 that specifies the joint portions 11 to be locked in accordance with the scaling ratio input from the input portion 15 and that activates the locking mechanisms of those joint portions 11 are provided as the scaling-ratio changing mechanisms 14.

In addition, in this embodiment, in the case in which the pivoting angle of the lever 13 is changed by activating the locking mechanisms, the control portion 6 changes the gain, by which the operation input level from the master device 2 is multiplied, so that the entire pivoting-angle range in that changed state corresponds to the entire bending-angle range of the bending portion of the endoscope 4.

The operation of the thus-configured master device 10 according to this embodiment will be described below.

Figure 7:
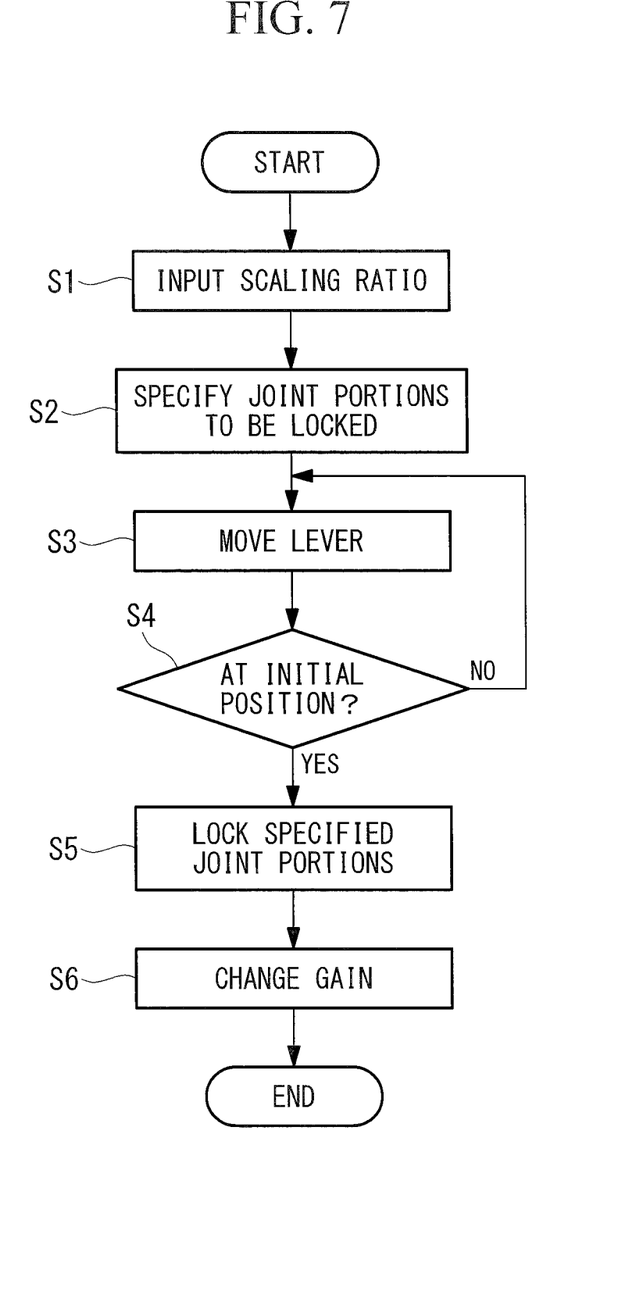
FIG. 7 is a flowchart for explaining the procedure for changing a scaling ratio in the operation input device in FIG. 4.

In order to switch the master device 10 according to this embodiment to the coarse-movement operation, the operator O inputs a scaling ratio via the input portion 15 (Step S1). The control portion 6 specifies the joint portions 11 to be locked in accordance with the input scaling ratio (Step S2).

Then, the operator O moves the lever 13 so as to bring it back to an initial position (position at which the pivoting angle is zero) (Step S3). The control portion 6 confirms whether or not the lever 13 has been brought back to the initial position (Step S4), and, in the case in which the lever 13 has been brought back to the initial position, activates the locking mechanisms of the joint portions 11 specified in accordance with the input scaling ratio (Step S5).

Figure 5:
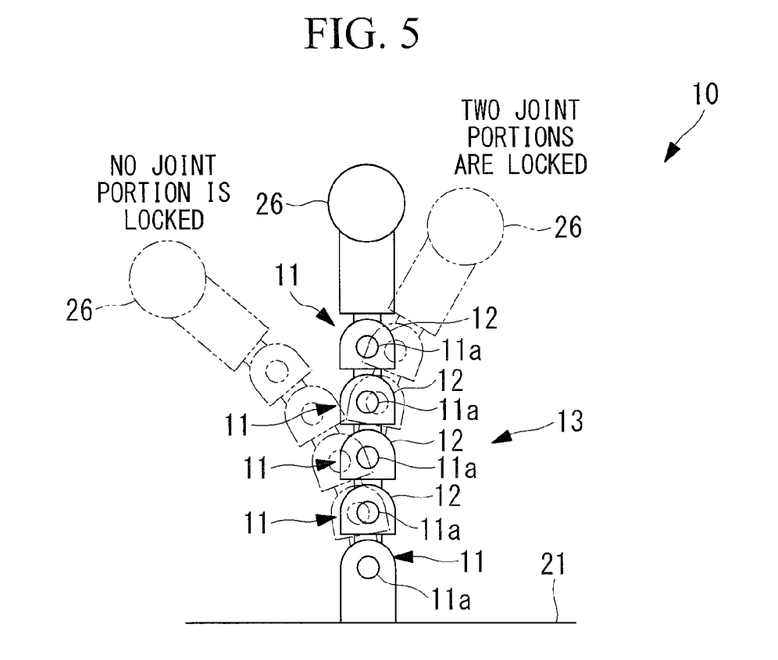
FIG. 5 is a front view for explaining the operation of the operation input device in FIG. 4.

Locks on all joint portions 11 are released in the state in which the scaling ratio is at a maximum, and, as the scaling ratio is decreased, the number of activated locking mechanisms is increased, starting from the joint portions 11 positioned closest to the base member 21. By doing so, because the number of joint portions 11 that can be pivoted is decreased when the scaling ratio is decreased, the pivoting-angle range is decreased even when a maximum level of pivoting is achieved.

Then, because the control portion 6 assigns this decreased pivoting-angle range to the bending-angle range of the bending portion of the endoscope 4 (Step S6), the grip 26 displaced by a small amount causes the bending portion to be bent by a large amount, and thus, the endoscope 4 can be moved coarsely.

In addition, by increasing the number of locked joint portions 11, the pivoting-angle range of the lever 13 is gradually decreased, and thus, the degree of the coarse movement can be increased.

In contrast, to switch the master device 2 to the fine-movement operation, the locked state of the joint portions 11 due to the locking mechanisms is released. By doing so, because it becomes possible to maximally pivot the lever 13, a large pivoting-angle range can be assigned to the bending-angle range of the bending portion of the endoscope 4, and, because the grip 26 displaced by a large amount causes the bending portion to be bent, the endoscope 4 can be moved finely.

Figure 8:
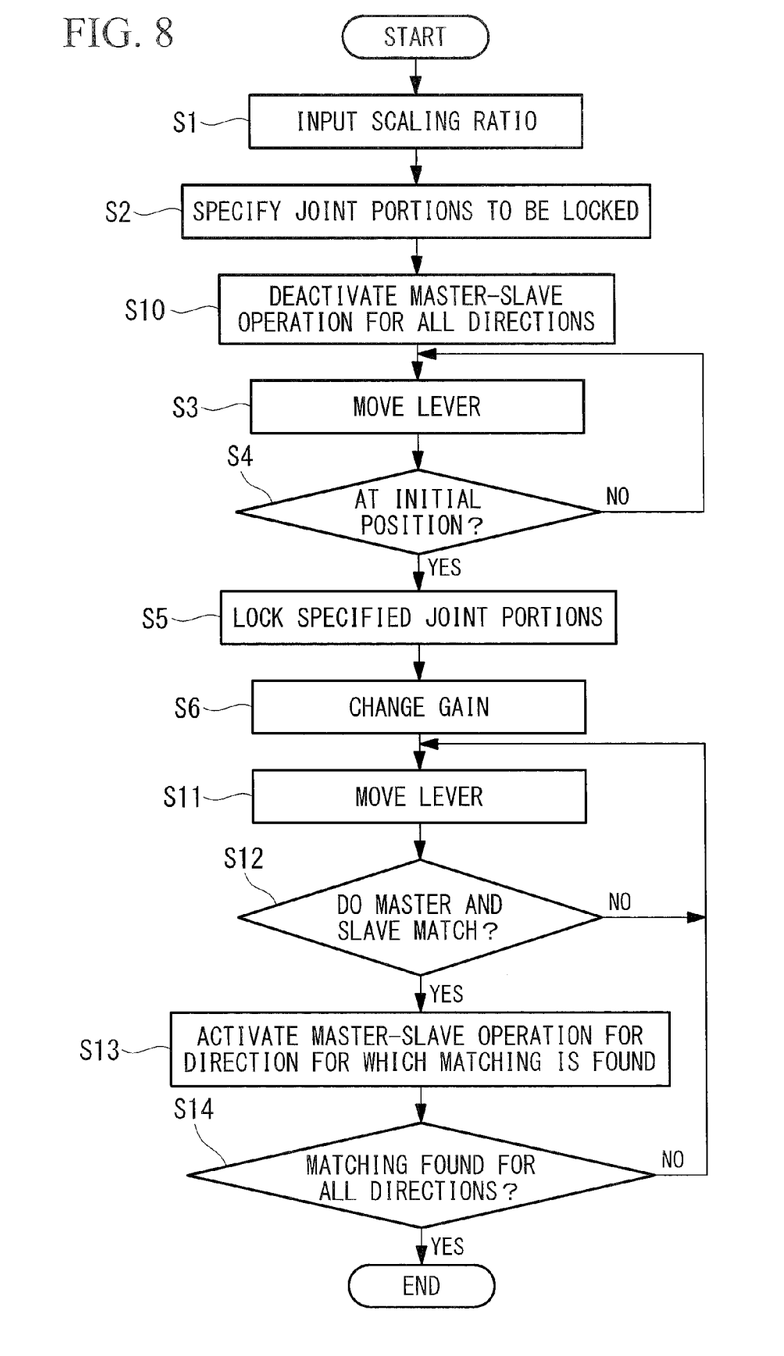
FIG. 8 is a flowchart for explaining another example of the procedure in FIG. 7.

In addition, in the above-described process, although the endoscope 4 is also brought back to the initial position when the master device 2 is brought back to the initial position when changing the scaling ratio, alternatively, the scaling ratio may be changed without bringing the endoscope 4 back to the initial position. In this case, as shown in FIG. 8, once the joint portions to be locked are specified (Step S2), master-slave operation is deactivated for all shafts (Step S10), so that the endoscope 4 does not move even if the master device 2 is operated.

In this state, the master device is brought back to the initial position (Steps S3 and S4), the joint portions are locked (Step S5), the gain is changed (Step S6), and, subsequently, the operator moves the lever (Step S11). At this time, the control portion judges whether or not the master device and the endoscope match at the individual shafts (Step S12), and activates master-slave operation for the matched shafts (Step S13). Whether or not the master device and the endoscope match is judged for all shafts (Step S14), the steps from Step S11 are repeated in the case in which they do not match, and the process is terminated when they are matched at all shafts.

By doing so, the scaling ratio can be changed without moving the endoscope 4.

In addition, in the case in which the individual joint portions 11 are provided with motors so that they can be moved to arbitrary positions in accordance with instructions from the control portion 6, the configuration thereof may be such that, after deactivating master-slave operation for all shafts, the master device is automatically moved to the initial position, joint portions are locked, and, subsequently, the master-slave operation is activated for all shafts after automatically moving the master device to a position that matches with the slave.

Figure 9:
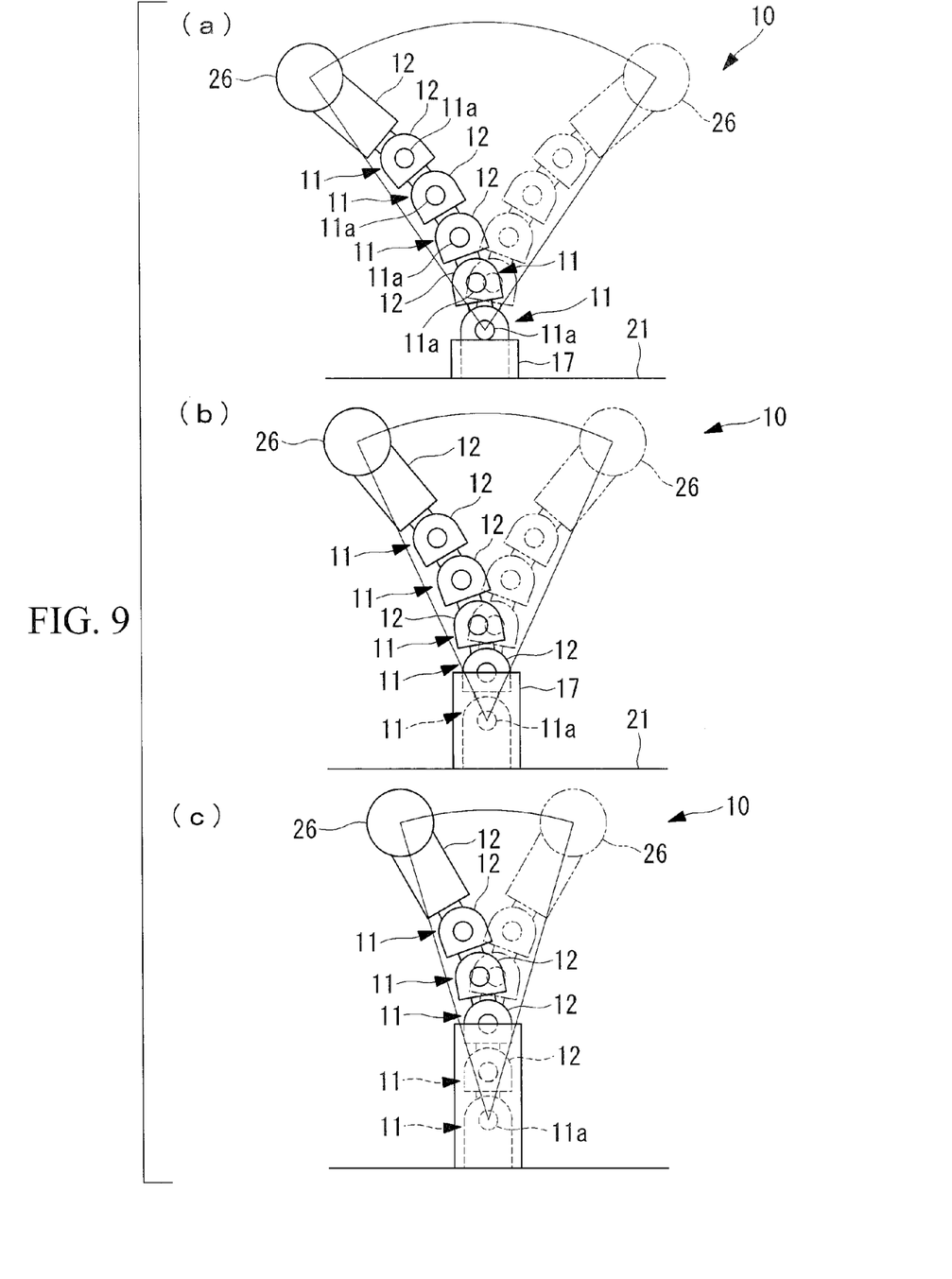
FIG. 9 is a front view for explaining states in which (a) joint portions are not locked, (b) only one joint portion is locked, and (c) two joint portions are locked, in a modification of the operation input device in FIG. 4.

Note that the locking mechanisms can be realized by activating brakes (not shown) provided at the individual joint portions 11 or by locking motors (not shown) provided in the individual joint portions 11. Alternatively, as shown in (a) to (c) in FIG. 9, the joint portions 11 may be locked from the base end of the lever 13 by means of a cylinder-shaped member 17 that can be made to protrude from and retracted into the base member 21.

Next, a master device 30 according to a third embodiment of the present invention will be described below with reference to the drawings.

In describing this embodiment, portions having the same configurations as those of the master devices 2 and 10 and the master-slave systems 1 according to the first and second embodiments described above will be assigned the same reference signs and descriptions thereof will be omitted.

Figure 10:
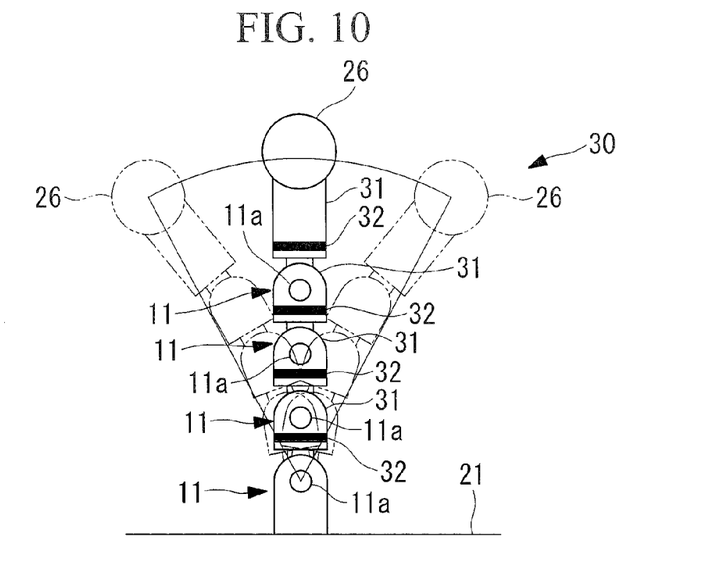
FIG. 10 is a front view of an operation input device according to a third embodiment of the present invention, showing a case in which a scaling ratio is decreased.
Figure 11:
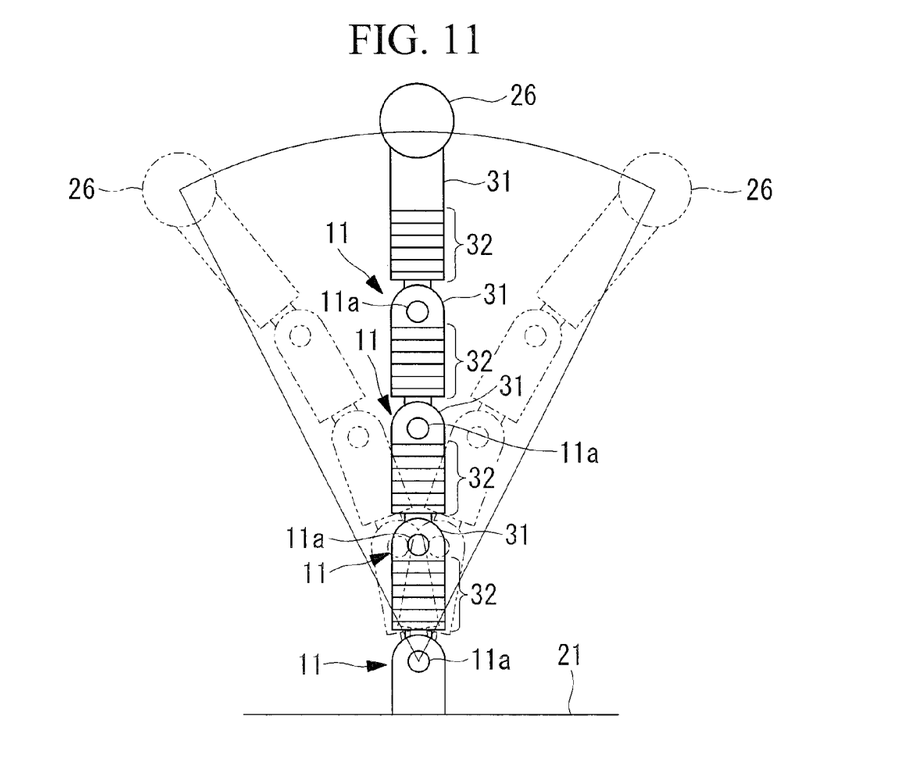
FIG. 11 is a front view of the operation input device in FIG. 10, showing a case in which the scaling ratio is increased.

As shown in FIGS. 10 and 11, in a master device 30 according to this embodiment, linkages 31 disposed between the plurality of joint portions 11 have extending/contracting portions 32 that can be extended/contracted in the axial direction. In the case in which the scaling ratio needs to be decreased, the extending/contracting portions 32 of the individual linkages 31 are contracted in accordance with the scaling ratio, as shown in FIG. 10, and, in the case in which the scaling ratio needs to be increased, the extending/contracting portions 32 of the linkages 31 are extended, as shown in FIG. 11. By doing so, as with the first and second embodiments, it is possible to switch between the coarse movement and the fine movement of the endoscope 4 by easily changing the scaling ratio.

In this case, with the master device 30 according to this embodiment, the scaling ratio can be changed merely by extending/contracting the extending/contracting portions 32 without changing the pivoting angles of the individual joint portions 11. As a result, the scaling ratio can be changed without having to bring back the joint portions 31 to the initial positions, and it is possible to prevent the endoscope 4 from moving without having to deactivate the master-slave operation when changing the scaling ratio.

Figure 12:
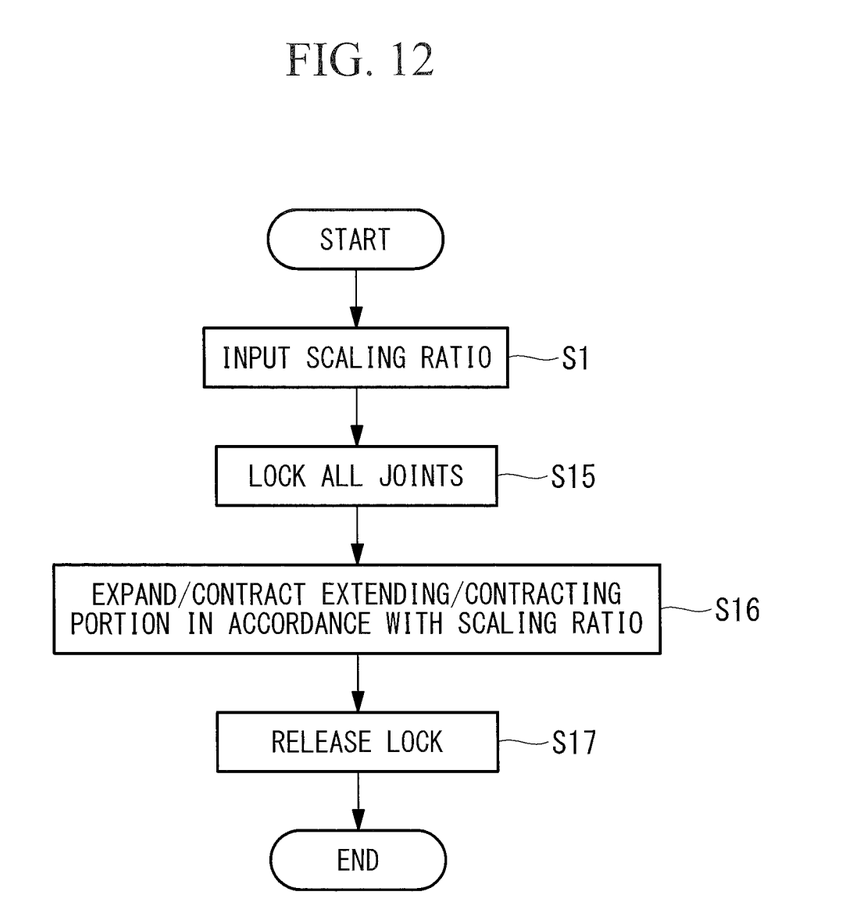
FIG. 12 is a flowchart for explaining the procedure for changing the scaling ratio in the operation input device in FIG. 10.

Note that, in order to more reliably perform movements involved in changing the scaling ratio, a configuration should be employed such that, as shown in FIG. 12, the joint portions 11 are locked by activating the locking mechanisms of all joint portions 11 (Step S15) once the scaling ratio is input (Step S1), after which the extending/contracting portions 32 are extended/contracted in accordance with the scaling ratio (Step S16), and, subsequently, the locking mechanisms of all joint portions 11 are released (Step S17). By doing so, because the master device 30 is not operated when changing the scaling ratio, it is possible to prevent the correspondence relationship between the master device 30 and the endoscope 4 from losing the correspondence therebetween before and after changing the scaling ratio.

The extending/contracting portions 32 may manually be extended/contracted, as in the first embodiment, or they may be extended/contracted by means of an arbitrary motive power, such as electric power, pneumatic pressure, and so forth.

In addition, in the individual embodiments described above, although the coupling portion having the joint portions 11 or 23 is employed, it is not limited thereto, and, for example, the coupling portion may be constituted of a self-supporting spring material or rubber material. In this case, for example, by detecting the pivoting angle thereof by mounting an FBG sensor to the coupling portion, the slave device can be moved in accordance with the detection result thereof.

In addition, in the individual embodiments described above, the scaling-ratio changing mechanisms 14 and 24 may be actuated by changing the scaling ratio by pressing a switch, such as the footswitch 25 or a switch or the like provided in the grip 26.

In addition, the following aspect is lead from the individual embodiments described above.

An aspect of the present invention provides an operation input device including a base member; a grip that is gripped by an operator and that is moved relative to the base member; a coupling portion that couples the grip to the base portion in a pivotable manner; and a scaling-ratio changing mechanism that changes an amount by which the grip is moved with respect to a pivoting angle of the coupling portion.

With this aspect, because the coupling portion is pivoted by a pivoting angle in accordance with the amount by which the grip is moved when the operator grips and moves the grip relative to the base portion, this pivoting angle can be output as the operation input level. In this case, by changing the amount by which the grip is moved with respect to the pivoting angle of the joint portion by actuating the scaling-ratio changing mechanism, it is possible to change the operation input level output with respect to the amount by which the grip is moved by the operator, that is, the scaling ratio. Specifically, in the case in which the slave device is driven in accordance with the operation input level, the slave device can be finely moved when the amount by which the operator must move the grip to output the same operation input level is increased by increasing the scaling ratio. In contrast, the slave device can be coarsely moved by decreasing the scaling ratio.

In the above-described aspect, the scaling-ratio changing mechanism may be an extending/contracting mechanism that allows the length of the coupling portion to be varied.

By doing so, in the case in which the length from the coupling portion to the grip is extended by actuating the extending/contracting mechanism, that is, the scaling-ratio changing mechanism, the scaling ratio can be increased as compared with the case in which the length is decreased. Specifically, when the scaling ratio is increased, because the operator must move the grip by a greater amount to output the same operation input level, as compared with the case in which the scaling ratio is decreased, the slave device can be finely moved in a simple manner. In contrast, when the scaling ratio is decreased, the operator needs to move the grip only by a small amount to output the same operation input level, and thus, the slave device can be coarsely moved in a simple manner.

In addition, in the above-described aspect, the coupling portion may be provided with one or more joint portions.

In addition, in the above-described aspect, a plurality of the joint portions may be disposed in series between the base member and the grip, and the scaling-ratio changing mechanism may be a locking mechanism that locks pivoting of at least one of the joint portions at the base-member side.

By doing so, when pivoting of the joint portions closer to the base member is locked by activating the locking mechanism, that is, the scaling-ratio changing mechanism, because the length of a portion that is pivoted is decreased by being restricted to the portion closer to the distal end than the joint portions locked by the locking mechanism are, the amount by which the grip is moved is decreased. As a result, the scaling ratio can be decreased. In contrast, when pivoting of the joint portions is allowed by releasing the locking mechanism, because the length of the portion that is pivoted is increased, the amount by which grip is moved is increased, and thus, the scaling ratio can be increased.

In addition, in the above-described aspect, a plurality of the joint portions may be disposed in series between the base member and the grip, linkage members that connect adjacent joint portions may be provided, and the extending/contracting mechanisms may be provided in the linkage members.

By doing so, when the lengths of the linkage members between adjacent joint portions are increased by actuating the extending/contracting mechanisms, the amount by which the grip is moved to output the same operation input level can be increased, and thus, the scaling ratio can be increased. On the other hand, by decreasing the lengths of the linkage members between the joint portions, the scaling ratio can be decreased.

In addition, another aspect of the present invention provides a master-slave system including any one of the above-described operation input devices and a slave device that is moved in accordance with the pivoting angle of the joint portion of the operation input device.

With this aspect, by changing a scaling ratio input from the operation input device, it is possible to switch the movement of the slave device to a coarse movement or to a fine movement in a simple manner.

REFERENCE SIGNS LIST

O operator
1 master-slave system
2, 10, 30 master device (operation input device)
4 endoscope (slave device)
11, 23 joint portion (coupling portion)
12, 31 linkage (linkage member)
14, 24 scaling-ratio changing mechanism
17 cylinder-shaped member (locking mechanism)
21 base member
26 grip
32 extending/contracting portion (extending/contracting mechanism)

The invention claimed is:

1. An operation input device comprising:
   a base member;
   a grip configured to be gripped by an operator and to move relative to the base member;
   a coupling portion comprising a plurality of joint portions disposed in series between the base member and the grip, wherein the plurality of joint portions are configured to couple the grip to the base member in a pivotable manner; and
   a locking mechanism configured to lock pivoting of at least one of the plurality of joint portions at a base-member side to change an amount by which the grip is moved with respect to a pivoting angle of the coupling portion.

2. The operation input device according to claim 1, further comprising:
   linkage members configured to connect adjacent joint portions among the plurality of joint portions, and
   wherein the linkage members comprise extending/contracting mechanisms configured to vary a length of the coupling portion.

3. A master-slave system comprising:
   an operation input device according to claim 1; and
   a slave device that is moved in accordance with the pivoting angle of the coupling portion of the operation input device.

* * * * *